US009364667B1

United States Patent
Dinsmoor et al.

(10) Patent No.: US 9,364,667 B1
(45) Date of Patent: Jun. 14, 2016

(54) POTENTIATING OR ELICITING AN EROTIC SENSATION IN A BODY USING ELECTROSTIMULATION

(71) Applicant: Elassia LLC, North Oaks, MN (US)

(72) Inventors: David A. Dinsmoor, North Oaks, MN (US); Eric H. Bonde, Minnetonka, MN (US)

( * ) Notice: Subject to any disclaimer, the term of this patent is extended or adjusted under 35 U.S.C. 154(b) by 0 days.

(21) Appl. No.: 14/675,548

(22) Filed: Mar. 31, 2015

Related U.S. Application Data

(60) Provisional application No. 61/973,172, filed on Mar. 31, 2014.

(51) Int. Cl.
*A61N 1/18* (2006.01)
*A61N 1/36* (2006.01)
*A61N 1/05* (2006.01)

(52) U.S. Cl.
CPC .......... *A61N 1/36007* (2013.01); *A61N 1/0521* (2013.01); *A61N 1/0524* (2013.01); *A61N 1/36014* (2013.01); *A61N 1/36128* (2013.01); *A61N 1/36135* (2013.01)

(58) Field of Classification Search
CPC ........... A61N 1/36007; A61N 1/36014; A61N 1/0521; A61N 1/0524; A61N 1/36135; A61N 1/36128
USPC .................... 607/39, 59, 62, 63, 72, 138, 143
See application file for complete search history.

(56) References Cited

U.S. PATENT DOCUMENTS

| 3,024,783 | A | 3/1962 | Timcke |
| 3,294,092 | A | 12/1966 | Landauer |
| 3,295,528 | A | 1/1967 | Masaki |

(Continued)

FOREIGN PATENT DOCUMENTS

| CA | 2319525 A1 | 8/1999 |
| DE | 202004017511 U1 | 4/2005 |

(Continued)

OTHER PUBLICATIONS

Geng, et al, "Impacts of selected stimulation patterns on the perception Threshold in electrocutaneous stimulation", Journal of Neuroengineering and Rehabilitation 2011, 8:9.

(Continued)

*Primary Examiner* — Christopher D Koharski
*Assistant Examiner* — Michael Carey
(74) *Attorney, Agent, or Firm* — Albert W. Watkins

(57) ABSTRACT

A system and method for potentiating or eliciting an erotic sensation in a body using electrostimulation includes a controller for producing an electrical stimulation signal and at least two electrodes. The electrodes are adapted for placement on a body surface, for which at least one of the electrodes is used to potentiate or elicit an erotic sensation in the body when conveying the electrical stimulation signal from the controller. The electrical stimulation signal is provided in an amount and manner incorporating a plurality of high frequency pre-pulses prior to, and of narrower pulse width than, a primary pulse in the electrostimulation signal that is adapted to optimize the erotic sensation by limiting both concomitant adverse sensation and habituation at the locus of electrostimulation. The method further increases and decreases the stimulation amplitude responsive to open circuit, short circuit, and target settings.

20 Claims, 9 Drawing Sheets

(56) References Cited

U.S. PATENT DOCUMENTS

| | | |
|---|---|---|
| 3,299,892 A | 1/1967 | Kendall et al. |
| 3,329,148 A | 7/1967 | Kendall |
| 3,650,276 A | 3/1972 | Burghele et al. |
| 3,735,756 A | 5/1973 | Richards et al. |
| 3,893,463 A | 7/1975 | Williams |
| 3,941,136 A | 3/1976 | Bucalo |
| 3,952,751 A | 4/1976 | Yarger |
| 3,983,881 A | 10/1976 | Wickham |
| 4,240,437 A | 12/1980 | Church |
| 4,279,256 A | 7/1981 | Bucalo |
| 4,319,584 A | 3/1982 | McCall |
| 4,324,253 A | 4/1982 | Greene et al. |
| 4,409,565 A | 10/1983 | Scherer |
| 4,431,000 A | 2/1984 | Butler et al. |
| 4,453,548 A | 6/1984 | Maurer et al. |
| 4,585,005 A | 4/1986 | Lue et al. |
| 4,620,543 A | 11/1986 | Heppenstall et al. |
| 4,640,286 A | 2/1987 | Thomson |
| 4,653,479 A | 3/1987 | Maurer |
| 4,690,142 A | 9/1987 | Ross et al. |
| 4,919,138 A | 4/1990 | Nordenstroom |
| 4,919,139 A | 4/1990 | Brodard |
| 4,926,879 A | 5/1990 | Sevrain et al. |
| 5,069,211 A | 12/1991 | Bartelt et al. |
| 5,070,873 A | 12/1991 | Graupe et al. |
| 5,107,835 A | 4/1992 | Thomas |
| 5,117,826 A | 6/1992 | Bartelt et al. |
| 5,183,041 A | 2/1993 | Toriu et al. |
| 5,571,118 A | 11/1996 | Boutos |
| 5,702,428 A | 12/1997 | Tippey et al. |
| 6,047,212 A | 4/2000 | Gliner et al. |
| 6,236,890 B1 | 5/2001 | Oldham |
| 6,438,418 B1 | 8/2002 | Swerdlow et al. |
| 6,493,580 B1 | 12/2002 | Cansell et al. |
| 6,526,319 B2 | 2/2003 | Kobayashi |
| 6,535,767 B1 | 3/2003 | Kronberg |
| 6,650,943 B1 | 11/2003 | Whitehurst et al. |
| 6,671,546 B2 | 12/2003 | Cansell et al. |
| 6,671,557 B1 | 12/2003 | Gliner |
| 6,684,106 B2 | 1/2004 | Herbst |
| 7,050,856 B2 | 5/2006 | Stypulkowski |
| 7,133,723 B2 | 11/2006 | Yu |
| 7,167,752 B2 | 1/2007 | Lin-Hendel |
| 7,191,014 B2 | 3/2007 | Kobayashi et al. |
| 7,333,858 B2 | 2/2008 | Killian et al. |
| 7,584,003 B2 | 9/2009 | Zanella |
| 7,593,775 B2 | 9/2009 | Campos et al. |
| 7,689,287 B2 | 3/2010 | Han |
| 7,890,182 B2 | 2/2011 | Parramon et al. |
| 7,979,137 B2 | 7/2011 | Tracey et al. |
| 8,073,544 B2 | 12/2011 | Pless |
| 8,165,695 B2 | 4/2012 | Diubaldi et al. |
| RE43,374 E | 5/2012 | Kronberg |
| 8,315,711 B2 | 11/2012 | Campos et al. |
| 2010/0204624 A1 | 8/2010 | Vuillerme et al. |
| 2012/0215141 A1* | 8/2012 | Peddicord ............ A61H 9/0078 601/46 |
| 2013/0237750 A1 | 9/2013 | Green |

FOREIGN PATENT DOCUMENTS

| | | |
|---|---|---|
| EP | 0620025 A1 | 10/1994 |
| EP | 0897706 A2 | 2/1999 |
| EP | 1916982 A2 | 8/2006 |
| WO | WO 2006063461 A1 | 6/2006 |

OTHER PUBLICATIONS

Scheibert J., Leurent S., Prevost A., Debregas G. (2009), "The role of fingerprints in the coding of tactile information probed with a biomimetic sensor", Science, 323(5920): 1503-6.

\* cited by examiner

POTENTIATING OR ELICITING AN EROTIC SENSATION IN A BODY USING ELECTROSTIMULATION

CROSS REFERENCE TO RELATED APPLICATIONS

The present application claims the benefit of U.S. provisional patent application 61/973,172 filed on Mar. 31, 2014 of like inventorship, the teachings and entire contents which are incorporated herein by reference.

BACKGROUND OF THE INVENTION

1. Field of the Invention

The present invention relates to a system and method employed to electrically stimulate body surfaces so as to potentiate or elicit erotic sensations.

2. Description of the Related Art

Since Luigi Galvani inferred that electric charge could be used to generate a response in excitable tissue in 1771, scientists, researchers and hobbyists have experimented with electricity as a means to evoke various electrophysiologically mediated responses. These responses include, but are not limited to, cardiac pacing and defibrillation, spinal cord stimulation (SCS), deep brain stimulation (DBS), peripheral nerve stimulation (PNS), transcutaneous neural stimulation (TENS), evoked myograms (EMG), erotic stimulation (e-stim), and sensory and motor prosthesis among many others.

The mechanism of action for electrostimulation-mediated sensation generation involves the use of applied electricity to modulate action potentials in the nervous system. Action potentials are depolarizations of neurons which are capable of propagating throughout the body. Inputs to the nervous system are provided by sensory receptors which transduce stimuli such as temperature, pain and touch. Two specific examples of sensory receptors are mechanoreceptors, which transduce mechanical deformation proximal to the receptor, and nociceptors, which transduce the sensation and response to pain. The nerve fibers originating from these sensory receptors terminate at specific points in the central nervous system, which in turn correspond to the signal being sensed. This sensory modality specific linkage is the so-called "labeled line principle." By means of example, if a touch fiber is stimulated by exciting a touch receptor electrically or in any other way, touch is perceived because the nervous pathway originating from the activated mechanoreceptor terminates in the touch area of the brain. An auditory sensation would not be perceived in this example, as the sensory receptor and pathway is specific for touch not auditory sensation.

Some exemplary mechanoreceptors are shown in FIG. 1. These mechanoreceptors include, but are not limited to, free nerve endings, expanded tip receptors, tactile hair sensors, Pacinian, Meissner's and Krause's corpuscles, Merkel's disks, Ruffini's end-organ, Golgi tendon apparati and muscle spindles. These receptors may be excited in one of several different ways. These methods for excitation may include an appropriate applied electrical stimuli, mechanical deformation or chemical excitation, among others. Each of these receptors are preferentially excited in a slightly different manner. For example, Meissner's corpuscles are selective to light touch at 30-50 Hz. Pacinian corpuscles are more selective to deeper, vibratory touch at 250-350 Hz. Merkel's disks respond to frequencies in the 5-15 Hz range. This non-painful sensory information is carried by large diameter (5 to 12 microns) alpha-beta fibers back to the dorsal horn of the spinal cord and eventually to the brain.

A characteristic of all sensory receptors is that they eventually habituate to some degree to their respective stimuli. When a continuous stimuli is applied, the receptors respond at an initially high rate, followed by a then progressively slower rate until many no longer fire. FIG. 2 shows the habituation of several types of receptors as a function of time, in response to supra-maximal electrical stimulation. The Pacinian corpuscle extinguishes within several hundred milliseconds whereas the Merkel's disk habituates to constant stimulation over the period of hours or days. Receptors with ultra-short habituation times are referred to as phasic receptors, and are responsible for transducing the rate at which change takes place.

A representative electrostimulation signal applied to a body surface so as to potentiate or elicit an erotic sensation is shown in FIG. 3. Biphasic stimulation consisting of a cathodic phase where charge flows out of the target body surface is followed by an anodic phase where charge flows into the body surface. Delivering the cathodic phase first, versus the anodic phase, generally results in lower stimulation amplitude needed to elicit a sensation. The application of a biphasic waveform is generally preferred as it limits undesirable electrochemistry which can result in tissue damage at the electrode-body surface interface. The stimulation is provided at a given site on the body surface with respect to at least a second body surface electrode located somewhere else on the body.

For some, electrostimulation on a body surface may generate a perception of pain. This perception may stem from a host of causes, including one or more of: (a) electrostimulation of sufficient strength to result in muscle contraction; (b) psychosomatic pain in response to the unique sensation of electrostimulation; (c) frank activation of a nociceptive neural circuit. When a nociceptive neural circuit is activated, small diameter neurons such as unmyelinated C fibers less than 2 microns in diameter and myelinated alpha-delta fibers, 2 to 5 microns in diameter, convey the pain sensation to the dorsal horn of the spinal cord and eventually to the brain.

Recognizing that electrostimulation may be used to potentiate or elicit an erotic sensation, some references in the art have elaborated systems and methods which electrically stimulate the genitalia for the purpose of generating sensation therein. These systems and methods are generally designed with limited understanding of the target tissue electroneurophysiology and suffer in turn from habituation to the electrostimulation, numbness and pain in the recipient.

There are a number of patents and publications that teach various components or systems that provide background knowledge and also provide evidence of novelty of the present invention. The teachings and contents of these documents are incorporated herein in entirety by reference, and include the following U.S. patents and published applications: U.S. Pat. No. 3,024,783 by Timcke, entitled "Vibration therapy apparatus"; U.S. Pat. No. 3,294,092 by Landauer, entitled "Therapeutic apparatus"; U.S. Pat. No. 3,295,528 by Masaki, entitled "Electrical therapeutic equipment"; U.S. Pat. No. 3,299,892 by Kendall et al, entitled "Therapeutic pulse generation, control and transmission circuit"; U.S. Pat. No. 3,329,148 by Kendall, entitled "Control of electrotherapeutic apparatus"; U.S. Pat. No. 3,650,276 by Burghele et al, entitled "Method and apparatus, including a flexible electrode, for the electric neurostimulation of the neurogenic bladder"; U.S. Pat. No. 3,735,756 by Richards et al, entitled "Duplex ultrasound generator and combined electrical muscle stimulator"; U.S. Pat. No. 3,893,463 by Williams, entitled "Dual channel stimulator"; U.S. Pat. No. 3,941,136 by Bucalo, entitled "Method for artificially inducing urination, defecation, or sexual excitation"; U.S. Pat. No. 3,952,751 by Yarger, entitled "High-performance electrotherapeutic apparatus"; U.S. Pat. No. 3,983,881 by Wickham, entitled "Muscle stimulator"; U.S. Pat. No. 4,240,437 by Church, entitled "Electric massage apparatus and method"; U.S. Pat. No. 4,279,256 by Bucalo, entitled "Nerve stimulation method"; U.S. Pat. No. 4,319,584 by McCall, entitled "Electrical pulse acupressure system"; U.S. Pat. No. 4,324,253 by Greene et al, entitled "Transcutaneous pain control and/or muscle stimulating apparatus"; U.S. Pat. No. 4,409,565 by Scherer, entitled "Circuit arrangement for producing a low frequency alternating current"; U.S. Pat. No. 4,431,000 by Butler et al, entitled "Transcutaneous nerve stimulator with pseusorandom pulse generator"; U.S. Pat. No. 4,453,548 by Maurer et al, entitled "Method of improving sensory tolerance with modulated nerve stimulator"; U.S. Pat. No. 4,585,005 by Lue et al, entitled "Method and pacemaker for stimulating penile erection"; U.S. Pat. No. 4,620,543 by Heppenstall et al, entitled "Enhanced fracture healing and muscle exercise through defined cycles of electric stimulation"; U.S. Pat. No. 4,640,286 by Thomson, entitled "Optimized nerve fiber stimulation"; U.S. Pat. No. 4,653,479 by Maurer, entitled "Interrupted drive limb motion apparatus"; U.S. Pat. No. 4,690,142 by Ross et al, entitled "Method and system for utilizing electro-neuro stimulation in a bio-feedback system"; U.S. Pat. No. 4,919,138 by Nordenstroom, entitled "Method and apparatus for supplying electric energy to biological tissue for simulating the physiological healing process"; U.S. Pat. No. 4,919,139 by Brodard, entitled "Electrical neuromuscular stimulation device"; U.S. Pat. No. 4,926,879 by Sevrain et al, entitled "Electro-tactile stimulator"; U.S. Pat. No. 5,069,211 by Bartelt et al, entitled "Microprocessor controlled electronic stimulating device having biphasic pulse output"; U.S. Pat. No. 5,070,873 by Graupe et al, entitled "Method of and apparatus for electrically stimulating quadriceps muscles of an upper motor unit paraplegic"; U.S. Pat. No. 5,107,835 by Thomas, entitled "Electrotherapeutic treatment"; U.S. Pat. No. 5,117,826 by Bartelt et al, entitled "Combined nerve fiber and body tissue stimulation apparatus and method"; U.S. Pat. No. 5,183,041 by Toriu et al, entitled "Transcutaneous electric nerve stimulator"; U.S. Pat. No. 5,571,118 by Boutos, entitled "Apparatus for stimulating penile, scrotal, anal vaginal and clitoral tissue"; U.S. Pat. No. 5,702,428 by Tippey et al, entitled "Electrical stimulation for treatment of incontinence and other neuro-muscular disorders"; U.S. Pat. No. 6,047,212 by Gliner et al, entitled "External defibrillator capable of delivering patient impedance compensated biphasic waveforms"; U.S. Pat. No. 6,236,890 by Oldham, entitled "Stimulation of muscles"; U.S. Pat. No. 6,438,418 by Swerdlow et al, entitled "Method and apparatus for reduction of pain from electric shock therapies"; U.S. Pat. No. 6,493,580 by Cansell et al, entitled "Impulses or a series of impulses for defibrillation and device to generate them"; U.S. Pat. No. 6,526,319 by Kobayashi, entitled "Living body stimulating apparatus"; U.S. Pat. No. 6,535,767 by Kronberg, entitled "Apparatus and method for bioelectric stimulation, healing acceleration and pain relief"; U.S. Pat. No. 6,650,943 by Whitehurst et al, entitled "Fully implantable neurostimulator for cavernous nerve stimulation as a therapy for erectile dysfunction and other sexual dysfunction"; U.S. Pat. No. 6,671,546 by Cansell et al, entitled "Impulses or a series of impulses for defibrillation and device to generate them"; U.S. Pat. No. 6,671,557 by Gliner, entitled "System and method for providing percutaneous electrical therapy"; U.S. Pat. No. 6,684,106 by Herbst, entitled "Method and electronic components for multi-functional electrical stimulation systems"; U.S. Pat. No. 7,050,856 by Stypulkowski, entitled "Variation of neural-stimulation parameters"; U.S. Pat. No. 7,133,723 by Yu, entitled "Device for enhancing cell metabolism"; U.S. Pat. No. 7,167,752 by Lin-Hendel, entitled "Electronic electrical and electro-magnetic health enhancement and stimulation device"; U.S. Pat. No. 7,191,014 by Kobayashi et al, entitled "Living body stimulating apparatus"; U.S. Pat. No. 7,333,858 by Killian et al, entitled "Pulse burst electrical stimulation of nerve or tissue fibers"; U.S. Pat. No. 7,584,003 by Zanella, entitled "Apparatus of electro-stimulation and relative data support"; U.S. Pat. No. 7,593,775 by Campos et al, entitled "Sports equipment with resonant muscle stimulator for developing muscle strength"; U.S. Pat. No. 7,689,287 by Han, entitled "Method of aiding smoking cessation"; U.S. Pat. No. 7,890,182 by Parramon et al, entitled "Current steering for an implantable stimulator device involving fractionalized stimulation pulses"; U.S. Pat. No. 7,979,137 by Tracey et al, entitled "System and method for nerve stimulation"; U.S. Pat. No. 8,073,544 by Pless, entitled "Neurostimulator involving stimulation strategies and process for using it"; U.S. Pat. No. 8,165,695 by DiUbaldi et al, entitled "System and method for selectively stimulating different body parts"; Re 43,374 by Kronberg, entitled "Apparatus and method for bioelectric stimulation, healing acceleration and pain relief"; U.S. Pat. No. 8,315,711 by Campos et al, entitled "Resonant muscle stimulator"; 2010/0204624 by Vuillerme et al, entitled "Endo-buccal device for tactile stimulation and actuation"; and 2013/0237750 by Green and granted as U.S. Pat. No. 8,998,796, entitled "Sexual Stimulation Device".

In addition to the aforementioned U.S. patents and published patent applications, the following additional patents and publications are also incorporated herein by reference: CA 2319525 by Kaczmarek et al, entitled "Tongue placed tactile output device"; EP 1916982 by Freebody, entitled "Skin surface stimulation using a matrix of controlled stimulation elements"; EP 0620025 by Kolen, entitled "Microprocessor-based nerve and muscle stimulator for localized application"; DE 202004017511 by Jobb, entitled "Sex toy with an electrode for erotic stimulation comprises an assembly of 2-core braided wire, latex strip, bent metal rods and Y cables"; WO 2006063461 by Murison, entitled "Electro-mechanical sexual stimulation device"; EP 0897706 by Ardatin, entitled "Vibrator with clitoris stimulator"; Geng, et al, "Impacts of selected stimulation patterns on the perception threshold in electrocutaneous stimulation", Journal of Neuroengineering and Rehabilitation 2011, 8:9; and Scheibert J., Leurent S., Prevost A., Debregas G. (2009), "The role of fingerprints in the coding of tactile information probed with a biomimetic sensor", Science, 323(5920): 1503-6. In addition, Webster's New Universal Unabridged Dictionary, Second Edition copyright 1983, is incorporated herein by reference in entirety for the definitions of words and terms used herein.

As taught by Geng et al. incorporated by reference herein above, the primary challenge for any tactile feedback system, including erotic stimulation systems, is the necessity to manage target tissue habituation to sustained stimulation, and to manage electrostimulator adaptation to target tissue impedance changes. The first of these, target tissue habituation to sustained stimulation, has already been discussed herein above with reference to FIG. 2. The second, managing electrostimulator adaptation to target tissue impedance changes, has to do with the efficacy and safety of the electrostimulator responsive to target tissue impedance changes. For exemplary purposes, if the electrostimulator is designed to produce a pulse train having a voltage independent of target tissue impedance, then substantially more current and energy will be delivered to the tissue when there is low impedance. Described another way, if for exemplary purpose the environment is warm and humid, sufficient to cause a person to perspire, then the tissue will have significantly lower impedance than in a cool and dry environment. This means an apparatus functioning properly on a warm and humid day may be completely non-functional on a cool and dry day. In an alternative, if the electrostimulator is instead configured to produce a pulse train having a constant current, then when there is significantly more impedance in the target tissue, such as on a cold and dry day or when the electrode is poorly affixed or in only poor or partial contact, the electrostimulator may ramp the voltage up substantially to maintain the target current flow. This can harm the target tissue as well. As noted, there are many factors that can affect the impedance of the target tissue, including levels of perspiration, extent or pressure of tissue contact, amount and composition of electrode gels or lubricants, and many other factors. Consequently, managing electrostimulator adaptation to target tissue impedance changes is critical and yet very difficult in the prior art.

As those of ordinary skill in the art will appreciate readily upon reading the Summary of the Invention, Detailed Description of the Preferred Embodiments and Claims set forth below, at least some of the devices and methods disclosed in the patents and publications listed herein above may be modified advantageously in accordance with the teachings of the present invention. The foregoing and other objects, features and advantages, which will now become more readily apparent by referring to the following specification, drawings and claims, are provided by the various embodiments of the present invention.

SUMMARY OF THE INVENTION

In a first manifestation, the invention is an electrostimulation apparatus. An electrical power source is coupled to an electrical signal generator. The signal generator operatively generates a biphasic electrostimulation signal having at least one parameter selected to potentiate an erotic sensation in a body. The biphasic electrostimulation signal has a primary pulse and a plurality of high frequency pre-pulses prior to, and of narrower pulse width than, the primary pulse so as to reduce concomitant adverse sensation and habituation at the locus of electrostimulation. At least one body surface electrode is adapted to operatively deliver the electrostimulation signal to at least one portion of a body. At least one additional electrode is adapted to operatively complete an electrical circuit between the at least one body surface electrode, the body, and the electrical signal generator. An impedance monitor is adapted to operatively measure an impedance between the at least one body surface electrode and the at least one additional electrode. A stimulation amplitude control is adapted to operatively decrease an electrostimulation amplitude of the biphasic electrostimulation signal applied to the body responsive to impedance indicative of an open circuit between the at least one body surface electrode and the at least one additional electrode.

In a second manifestation, the invention is a method of potentiating an erotic sensation in a body using electrostimulation. In accord with the method, a biphasic electrostimulation signal is generated having one or more parameters selected to potentiate or elicit an erotic sensation in a body. A plurality of high frequency pre-pulses are incorporated prior to, and of narrower pulse width than, a primary pulse in the electrostimulation signal so as to reduce concomitant adverse sensation or habituation at the locus of electrostimulation. The electrostimulation signal is delivered to one or more portions of a body via at least a body surface electrode, positionable, secured or attached to or on a body surface.

OBJECTS OF THE INVENTION

Exemplary embodiments of the present invention solve inadequacies of the prior art by applying one or more electrical stimulation signals to one or more appropriate portions of a body surface in a manner effective to potentiate or elicit an erotic sensation in the body. The at least one electrical signal is applied by a controller that has at least two electrodes, positionable, secured or attached to or on a body surface. In one embodiment of the present invention, the electrical stimulation signal is adapted to potentiate or elicit an erotic sensation substantially free from sensory habituation proximal to the at least one of the electrodes. In another embodiment of the present invention, the electrical stimulation signal is adapted to potentiate or elicit an erotic sensation substantially free from concomitant pain proximal to the at least one of the electrodes.

The present invention and the preferred and alternative embodiments have been developed with a number of objectives in mind. While not all of these objectives are found in every embodiment, these objectives nevertheless provide a sense of the general intent and the many possible benefits that are available from embodiments of the present invention.

A first object of the invention is to provide solutions to one or more problems existing in the prior art respecting conventional systems and methods for potentiating or eliciting an erotic sensation in a body with electrostimulation, including one or more of: (a) painful, inappropriate or otherwise unwelcome sensation during or after electrostimulation; (b) habituation to the electrostimulation; (c) discontinuance by the user of the electrostimulation system for the reasons listed herein above. A second object of the invention is to provide targeted delivery of electrostimulation. Another object of the present invention is to provide an ability to change the electrostimulation delivered on-demand, instantaneously or under automatic control of the electrostimulation system. A further object of the invention is to incorporate multiple methods of feedback control for optimizing the electrostimulation (e.g., target tissue impedance, time-dependent, user activated). Yet another object of the present invention is to elicit a more acceptable and/or enjoyable erotic sensation by the recipient.

BRIEF DESCRIPTION OF THE DRAWINGS

The foregoing and other objects, advantages, and novel features of the present invention will be more readily understood and appreciated by reference to the following detailed description of the preferred embodiments thereof, taken in conjunction with the accompanying drawings, in which like reference numerals indicate identical structures throughout the several views, and wherein.

DESCRIPTION OF EXEMPLARY EMBODIMENTS OF THE PRESENT INVENTION

In the following descriptions of the preferred embodiments, reference is made to the accompanying drawings that form a part hereof, and in which are shown by way of illustration several specific embodiments of the invention. It is to be understood that other embodiments of the present invention are contemplated and may be made without departing from the scope or spirit of the present invention. The following detailed description, therefore, is not to be taken in a limiting sense. Instead, the scope of the present invention is to be defined in accordance with the appended claims.

In the present invention, electrical stimulation of appropriate body surfaces, more about which we say below, potentiates or elicits an erotic sensation and may also be employed as a sensory analogue. Action potentials generated by electrical stimulation of sensory mechanoreceptors and other neural structures distributed throughout the body travel by means of afferent pathways to structures in the central nervous system responsible for distributing, aggregating, interpreting and processing such tactile sensations. Specifically contemplated as a body surface in the present invention are those portions of the human body to which an electrical connection may be made without introducing an artificial orifice in the body. The hands, feet, lips, face, mouth, breasts, anus, rectum and genitalia are suitable for making electrical connections and are richly endowed with Merkel's disks and Pacinian corpuscles, among other exemplary somatic sensory endings. The female vulva and vagina are particularly well suited as body surface locations where erotic sensations may be potentiated or elicited with electrostimulation.

Figure 1:
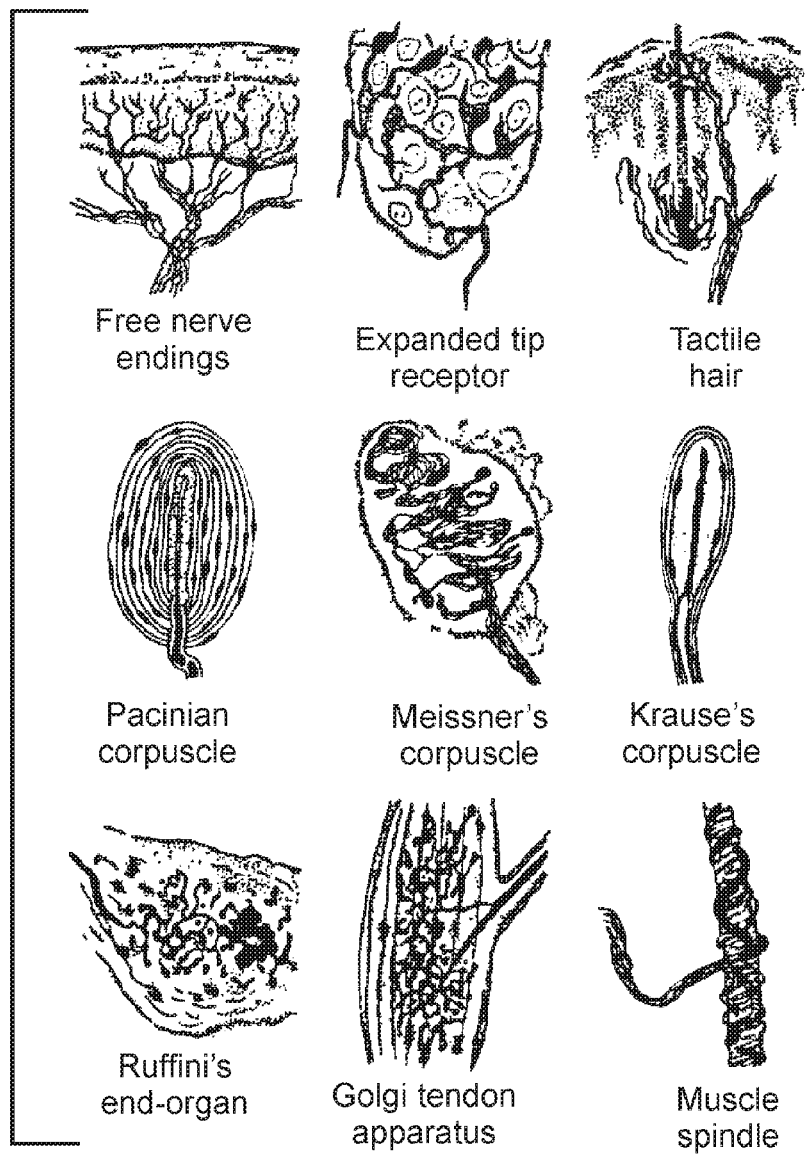
FIG. 1 illustrates a view of various prior art somatic sensory nerve endings.
Figure 2:
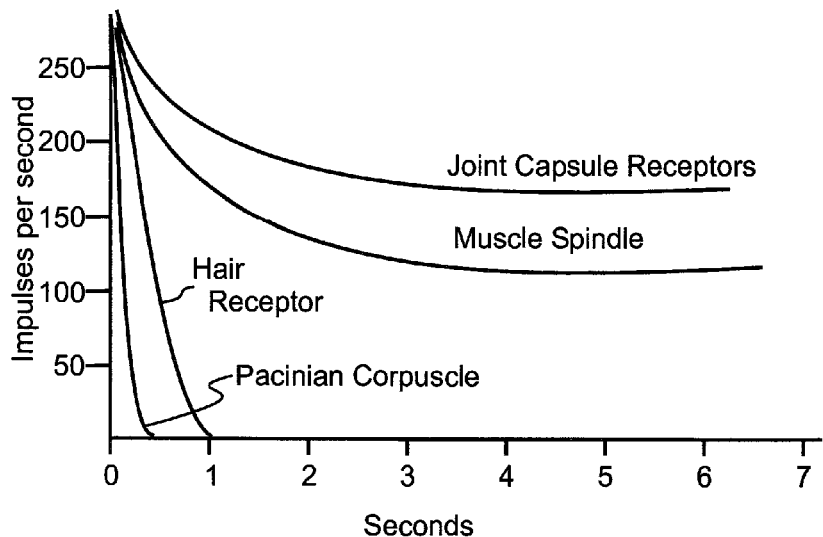
FIG. 2 illustrates the prior art habituation of different exemplary mechanoreceptors, showing rapid adaptation of some receptors and slow adaptation of others.
Figure 3:
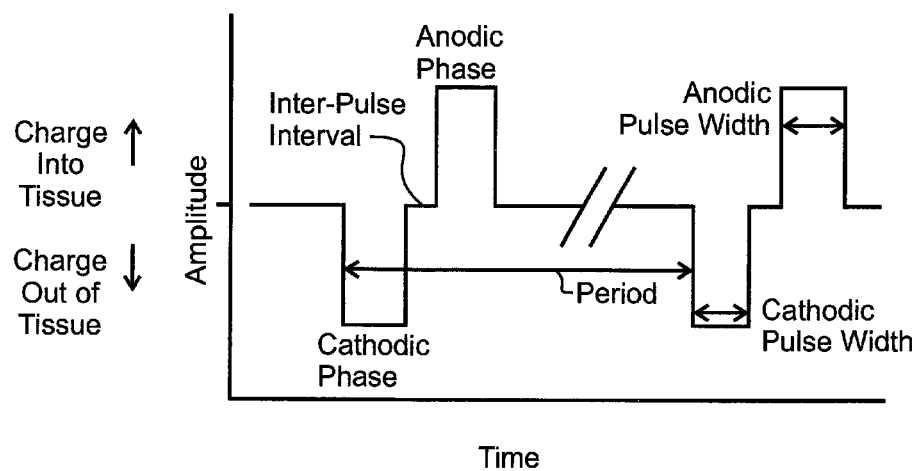
FIG. 3 depicts a representative prior art electrostimulation signal.
Figure 4:
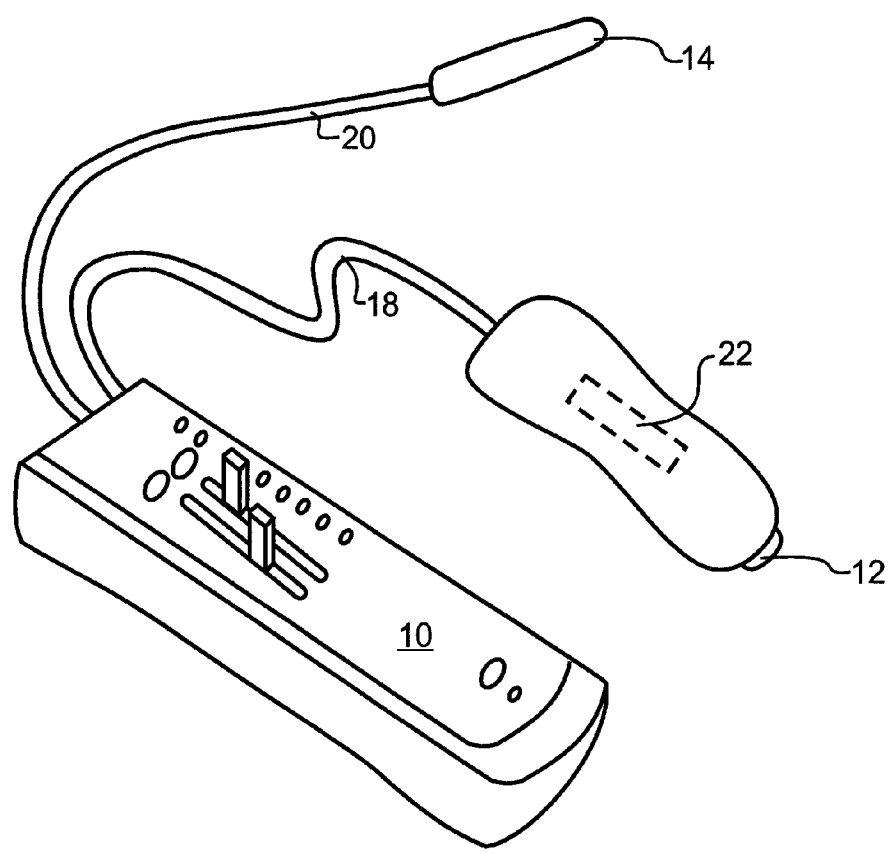
FIG. 4 shows illustrative apparatus used in one embodiment of the present invention for potentiating or eliciting an erotic sensation with an electrostimulation.
Figure 5A:
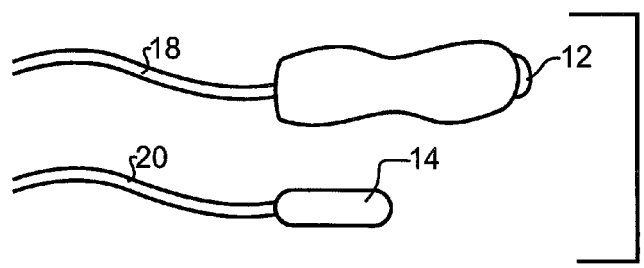
FIGS. 5a through 5f illustrate various alternative embodiment electrodes operative with the apparatus of FIG. 4.
Figure 5B:
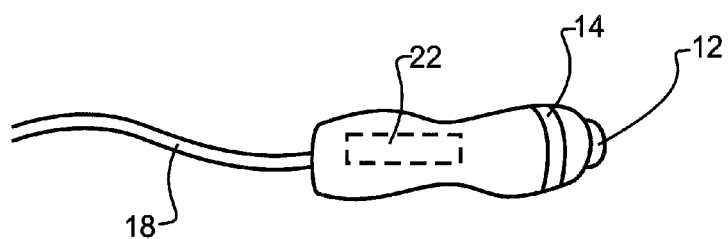
Figure 5C:
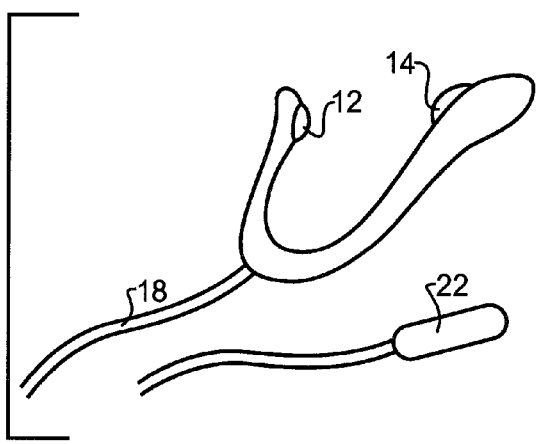
Figure 5D:
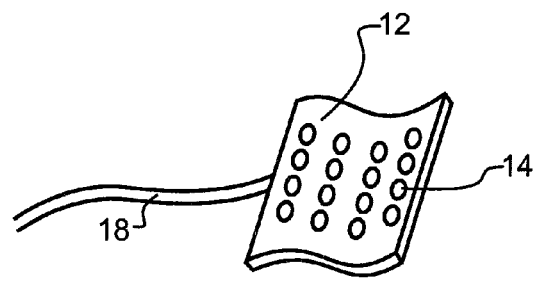
Figure 5E:
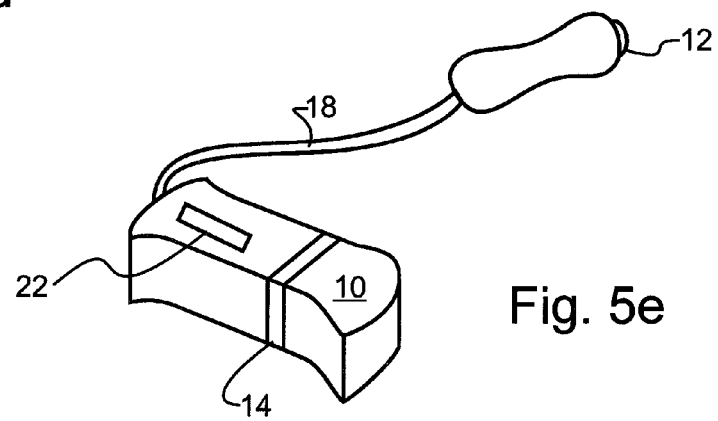
Figure 5F:
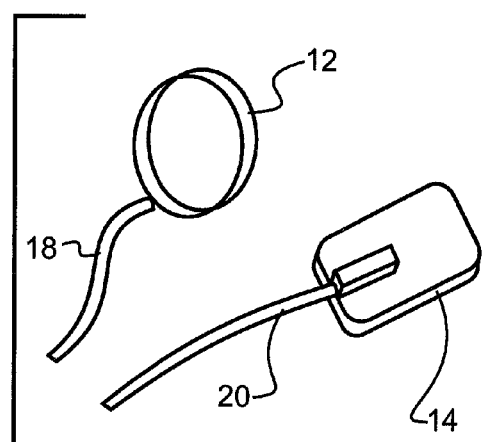

Referring to FIG. 4 and FIGS. 5*a* through 5*f*, electrodes 12 and 14 provide an electrical stimulation signal to the desired nerve target sites or portions and thereby inhibit or excite signals originating in or carried by a desired or target nerve portion located in the vicinity of the electrode(s) thereof. Electrodes 12, 14 may be disposed in common on lead 18 such as illustrated in FIGS. 5*b*, 5*c*, and 5*d*, on separate leads 18 and 20 such as illustrated in FIGS. 5*a* and 5*f*, on the housing of controller 10 such as illustrated in FIG. 5*e*, or a combination thereof. In some embodiments of the present invention such as illustrated in FIGS. 5*a* and 5*f*, electrode 12 is disposed on the distal terminus of lead 18, electrode 14 is disposed on the distal terminus of lead 20, and the lead conductors make an electrical connection from 12 and 14 to controller 10 at the proximal terminus of the leads.

Leads 18 and 20 are preferably insulated with polyurethane, although other suitable materials may be employed, for exemplary and non-limiting purpose including polyvinyl chloride, polyethylene, nylon, Teflon® polytetrafluoroethylene, rubber, latex and silicone. Electrical conductors between the proximal and distal ends of leads 18 and 20 for supplying electrical current to the electrodes may for exemplary and non-limiting purposes be formed of coiled, braided or stranded wires comprised of copper to provide good flexure and longer life. Other conductors, including but not limited to aluminum, metal-filled polymers, and other conductive compositions may also be used in some embodiments. Electrodes 12 and 14 may be spherical, cylindrical, round, or may assume any of a number of different structural configurations. The surface areas of electrodes 12 and 14 may preferably range between 1.0 sq. mm and about 200 sq. cm., more preferably range between 10 sq. mm and 100 sq. cm., and most preferably range between about 1 sq. cm and 50 sq. cm. Electrodes 12 and 14 are preferably formed of stainless steel, although other materials such as aluminum, platinum, gold or other suitable compositions may be employed. A suitably conductive gel, personal lubricant or adhesive such K-Y® Jelly, Astroglide® or OneStep EEG-Gel® may be used at the interface between electrodes 12 and 14 and body 6. Leads 18 and 20 preferably range between about 4 inches and about 20 inches in length, and more particularly may be about 6 inches, about 8 inches, about 10 inches, about 12 inches, about 14 inches, about 16 inches, or about 18 inches in length, depending on the location of the target 8 to be stimulated and a convenient location of the controller 10. Other lead lengths such as less than about 4 inches and more than about 20 inches are also contemplated in the present invention.

Electrode and lead configurations, arrays, and methods similar to those disclosed by Boutos in U.S. Pat. No. 5,571,118 entitled "Apparatus for stimulating penile, scrotal, anal vaginal and clitoral tissue;" by Green in US published application 2013/237750 and granted as U.S. Pat. No. 8,998,796 entitled "Sexual Stimulation Device;" by Jobb in DE202004017511 entitled "Sex toy with an electrode for erotic stimulation comprises an assembly of 2-core braided wire, latex strip, bent metal rods and Y cables"; and by Sevrain et al. in U.S. Pat. No. 4,926,879 entitled "Electro-tactile stimulator," the respective entireties of which are incorporated by reference herein above, may also be adapted or modified for use in the present invention for relaying an electrical stimulation signal to a body surface. Thus, although the Figures show certain electrode and lead configurations, other lead and electrode configurations are possible and contemplated in the present invention.

In other embodiments of the present invention, such as illustrated in FIGS. 5*b*, 5*c*, and 5*e* for exemplary purpose, at least one vibrating element 22 is adapted to lie on, adjacent or proximal to a nerve target 8. The vibrating element may also be adapted to lie on, adjacent or proximal to another nerve target or multiple nerve targets thereby. Vibrating motors such as the Precision Microdrives™ Pico-Vibe are especially suited for this purpose. Vibrating element 22 may be disposed on or in conjunction with leads 18 or 20 or adapted to lie in or on the housing of controller 10. Apparati which vibrate in such a manner are disclosed in EP 0897706 to Ardatin entitled "Vibrator with Clitoris Stimulator" and WO 2006/063461 to Murison entitled "Electro-mechanical sexual stimulation device," each of which are incorporated by reference herein above.

Figure 6:
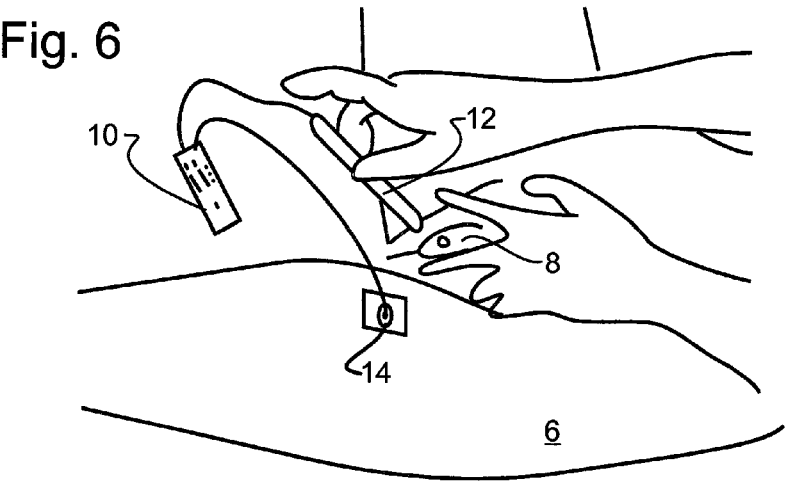
FIG. 6 illustrates one suitable arrangement of the present invention for potentiating or eliciting an erotic sensation with electrostimulation.

FIG. 6 shows an exemplary environment of a system for potentiating or eliciting an erotic sensation of the present invention. The body 6 depiction shows a female torso, a vulva 8 and a vagina. A user operates controller 10 to deliver an electrical stimulation signal to body surface electrodes 12, 14. In the illustrated embodiment, a user and body 6 are one person, although the user and body 6 may also be of separate identity. The controller 10 may also be in communication with another device such as personal computer, laptop, personal digital assistant, tablet, smart phone, hub, internet or cloud connected appliance, recharger or any other similar device well known in the art.

FIG. 6 further shows one embodiment of controller 10 of the present invention having electrodes 12, 14 positioned near a desired sensory receptor, receptors, nerve target, targets or portion thereof 8 on body 6. Controller 10 is a neural electrostimulator and is in electrical communication with one body surface electrode 12 and a second body surface electrode 14. In accord with certain embodiments of the present invention, at least one more body surface electrode similar to electrodes 12, 14 may be employed, where multiple nerve or receptor target sites or portions are to be stimulated simultaneously or sequentially and/or where such multiple target sites or portions are incapable of being stimulated, or are difficult to stimulate, using a single pair of electrodes 12, 14.

Figure 7:
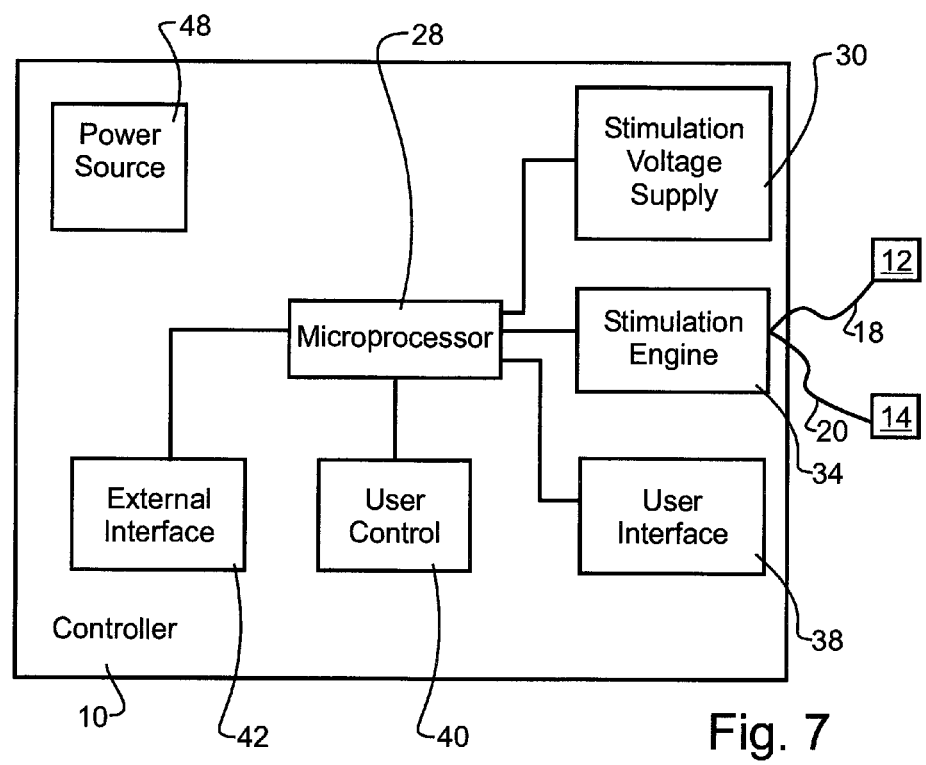
FIG. 7 illustrates an electrical block diagram of one embodiment of an electrostimulator controller used in an exemplary embodiment of the present invention.

Referring now to FIG. 7, illustrated therein is a block diagram of some constituent components of controller 10 in accordance with one embodiment of the present invention, wherein controller 10 has a microprocessor 28-based electrical architecture. The Microchip® PIC16LF1824 is well-suited to be used as microcontroller 28. Other architectures of controller 10 are of course contemplated such as the discrete implementation described by Bucalo, U.S. Pat. No. 3,941,136, entitled "Method for artificially inducing urination, defecation, or sexual excitation," incorporated by reference herein above, in its entirety. Stimulation voltage supply 30 may be a boost regulator, a charge pump, a capacitive voltage divider, a buck-boost regulator, a buck regulator, a shunt regulator, a low drop-out regulator, an unregulated power source or any of a number of different circuit architectures well known in the art of voltage supply. In the preferred embodiment, stimulation engine 34 uses the voltage made available by the stimulation voltage supply 30 to sink or source controlled charge in a multi-programmable fashion from at least one of body surface electrodes 12 and 14. For the sake of clarity, electrodes 12 and 14 are shown disposed on separate leads 18 and 20, although other lead and electrode configurations are contemplated and considered in the present invention. Also considered in the present invention is a stimulation engine 34 wherein a controlled voltage or current is delivered. The specific embodiments of such a stimulation engine and stimulation voltage supply are presented for illustrative purposes only, and are not intended to be limiting in respect of the scope of the present invention. The specific embodiments of such circuits may not be critical to practicing some embodiments of the present invention so long as they provide means for generating an appropriate electrical stimulation signal to the desired nerve target.

In the preferred embodiment, user interface 38 provides feedback to a user such as body 6 regarding the configuration, status, operation and behavior of the system for potentiating or eliciting an erotic sensation in body 6. In accordance with various embodiments of the present invention, some of the following may preferentially be provided to a user: power supply capacity and status, impedance from electrode to electrode, electrostimulation program, electrostimulation amplitude, vibration program, vibration intensity, wireless communication status, connection status and error status. User control 40 may be composed of buttons, switches, sliders, joysticks, touch screens or any other of a number of elements known in the art of electronics user interfaces for configuring the behavior of an electrical or electronic system. In some embodiments of the present invention, a further means of relaying data and control information is provided via external interface 42. External interface 42 may for exemplary and non-limiting purposes provide a series of encoded signals to and from controller 10, and more preferentially to and from microcontroller 28 incorporated in controller 10. One such external interface is the LS Research TiWi-BLE module. Another external interface is the Blue Radios® BR-LE4.0-S2A. Yet another suitable interface is a wired USB link to a host PC. Any of a number of suitable communication methodologies known in the art of electrical and electronic communications may be employed so long as the desired information is transmitted to and from controller 10.

Figure 8:
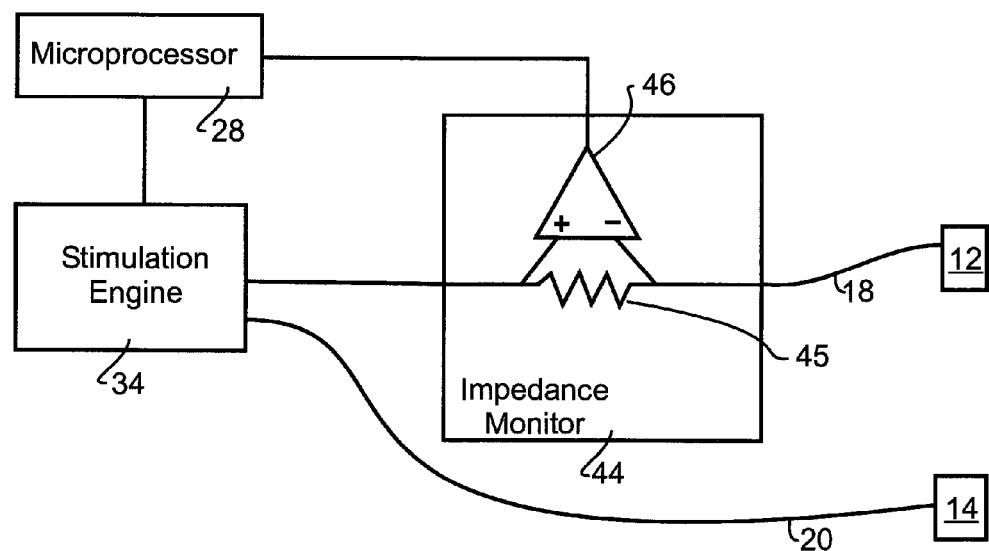
FIG. 8 illustrates an electrical block diagram of one embodiment of an impedance detection system used in an exemplary embodiment of the present invention.

The impedance between body surface electrodes 12, 14 may also be monitored, with the resultant data fed back to a user, adapted to servo the behavior of the electronics included in controller 10, or a combination thereof. Impedance monitor 44 uses any number of different techniques known in the electrical arts to measure the impedance between at least body surface and electrodes 12 and 14. In one embodiment of the present invention depicted in FIG. 8, a sense resistor 45 is included in series with the output of stimulation engine 34. A differential amplifier 46 is adapted to monitor the voltage drop during electrostimulation across sense resistor 45, wherein the value of sense resistor 45 is known to be much less than the resistance between the body surface electrodes. The output of differential amplifier 46 is then fed back to microprocessor 28 where the voltage is sampled and digitized by an analog-to-digital converter incorporated within or otherwise electrically coupled with microprocessor 28. The value of sense resistor 45 may then be divided into the digital representation of the output of differential amplifier 46, so as to infer the current flowing through sense resistor 45 and, in turn, the current flowing through the desired sensory receptor, receptors, nerve target, targets or portion thereof 8 on a body 6. This calculated current may then be divided into the amplitude of the stimulation signal from stimulation engine 34 to determine the impedance of the targeted electrostimulation target 8. A "short circuit" condition may be construed to exist when the impedance between any two body surface electrodes is in one embodiment between about 0.01 ohms and 1000 ohms, in a more particular embodiment between about 0.1 ohms and 100 ohms, or in a most particular embodiment between about 1 ohm and 50 ohms. An "open circuit" condition may be construed to exist when the impedance between any two body surface electrodes is in one embodiment greater than 1 kilo-ohm, in a more particular embodiment greater than 10 kilo-ohms, in an even more particular embodiment greater than 100 kilo-ohms, or in a most particular embodiment greater than about 1 mega-ohm.

Electrical or electro-mechanical components incorporated in or in electrical communication with controller 10 may be powered by power source 48, which may be a primary (i.e., non-rechargeable) battery or batteries, or secondary battery (i.e., rechargeable) battery or batteries. The power source may also be provided from an external source such as a the +5V supply of a USB port, or an AC/DC adaptor. One AC/DC adaptor suitable for use is the Simply Monitored DC12V 1A Power Adapter. It is generally preferred that the power source 48 is isolated from AC mains for the safety of body 6. Numerous other electrostimulation controller functions and features not explicitly mentioned herein may be incorporated into controller 10 while remaining within the scope of the present invention.

Figure 9:
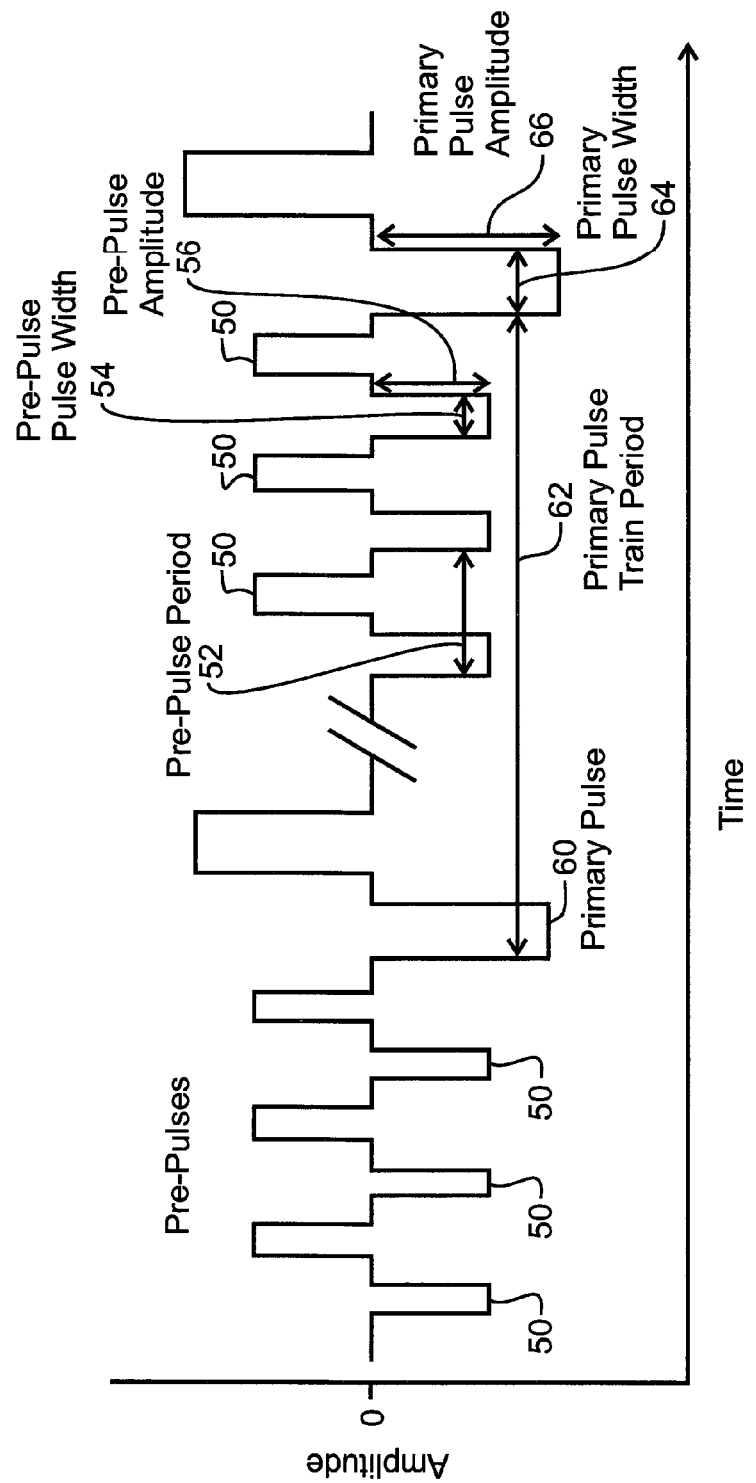
FIG. 9 depicts one embodiment of an electrostimulation signal used in one embodiment of the present invention.

We turn our attention now to the electrical stimulation signal delivered to a target 8 from stimulation engine 34, as shown in FIG. 9. Although the pulses forming the electrical stimulation signal are depicted with a square morphology in the Figures, the morphology of the pulse may be a triangle, sinusoid, gaussian, exponential, ramp, or any morphology or combination thereof known in the electrical art as long as it is biphasic and serves to deliver charge to and from target 8. In one embodiment of the present invention, a plurality of biphasic pre-pulses 50 with a shorter period 52 than that of a primary pulse 60 are applied to at least a body surface electrode 12 and 14 to limit pain and adverse sensation at the locus of electrostimulation. The delivery of pre-pulses in high-voltage cardiac defibrillation applications so as to limit pain is described by Swerdlow, U.S. Pat. No. 6,438,418, entitled "Method and apparatus for reduction of pain from electric shock therapies," incorporated by reference herein above.

In the preferred embodiment, the electrical stimulation signal is applied to one of either body surface electrode 12 or 14, with the other body surface electrode that is not driven by the electrical stimulation signal connected to a convenient reference voltage such as battery ground. Contemplated of course by the present invention is the application of an electrical stimulation signal to more than one body surface electrode, as noted herein above. The number of pre-pulses 50 in one embodiment range between 2 and 50, more particularly between 3 and 30, in a more specific embodiment between 4 and 20, and in an even more particular embodiment between 5 and 10. One pre-pulse and a number of pre-pulses larger than 50 are also considered in the present invention. The period 52 of the pre-pulses 50 may be fixed or variable. In some embodiments, the inverse of period 52 (e.g., the frequency of any two adjacent pulses in the pre-pulse train) may be between 300 Hz and 30 kHz, between 500 Hz and 25 kHz, or between 1 kHz and 10 kHz. For the sake of clarity, the period 52 is depicted between two arbitrary pulses. The pulse width 54 of each phase of the pre-pulse may be fixed or variable, and may have asymmetrical pulse widths for the anodic and cathodic phases. For the sake of clarity, the pulse width 54 is shown only on the single phase of a pulse but applies independently to all phases of pulse train 50. The pulse width may in one embodiment be between 5 microseconds and 200 microseconds, in a more specific embodiment be between 8 microseconds and 100 microseconds, in an even more specific embodiment be between 10 microseconds and 50 microseconds, and in one particular embodiment be about 20 microseconds. An inter-pulse interval where no charge is delivered to the nerve target 8 between adjacent cathodic and anodic phases may be employed. Of course, the sum of the pulse width for an adjacent cathodic and anodic phase, plus any inter-pulse interval, cannot exceed the period 52 of the respective biphasic pulses. The amplitude 56 of the pre-pulse train may vary between 100 microamperes and 50 milliamperes, between 200 microamperes and 20 milliamperes and between 500 microamperes and 5 milliamperes. The amplitude 56 may be fixed or vary. In some embodiments of the present invention, the amplitude of the cathodic and anodic phases may differ.

The primary pulse train 60 has a period 62 selected to preferentially activate the target neural structure 8 and potentiate or elicit an erotic sensation thereby. The inverse of period 62 (e.g., the frequency) of any two adjacent pulses in primary pulse train 60 may in one exemplary embodiment be between 1 Hz and 1 kHz, in a preferred embodiment be between 5 Hz and 500 Hz, and in a most preferred embodiment be between 10 Hz and 300 Hz. Frequencies slower than 1 Hz and faster than 1 kHz are of course contemplated in the present invention. The period 62 may be fixed or variable. For the sake of clarity, the period 62 is depicted between two arbitrary pulses. In some embodiments, period 62 is random, pseudo-random or constrained to vary within a certain range. In accordance with some embodiments of the present invention, a linear-feedback shift register is used to add or subtract pseudo-random variation onto the primary pulse train period 62. The pulse width 64 of each phase of the primary pulse may be fixed or variable, and may have asymmetrical pulse widths for the anodic and cathodic phases. For the sake of clarity, the pulse width 64 is only shown on the cathodic phase of one biphasic pulse of 60, but may apply to the anodic phase as well. The pulse width in one exemplary embodiment may be between 10 microseconds and 5 ms, in a preferred embodiment may be between 50 microseconds and 1 millisecond, in a more preferred embodiment may be between 100 microseconds and 500 microseconds, and in a most preferred embodiment may be about 200 microseconds. An inter-pulse interval where no charge is delivered to the nerve target 8 between adjacent cathodic and anodic phases may be employed. Of course, the sum of the pulse width for an adjacent cathodic and anodic phase cannot exceed the period 62 of the respective biphasic pulse. Further, the sum of the pulse width for an adjacent cathodic and anodic phase, plus any inter-pulse interval, must be sufficiently short to allow time for the delivery of the pre-pulse train 50. The amplitude 66 of the primary pulse train in an exemplary embodiment may vary between 100 microamperes and 50 milliamperes, in a preferred embodiment may vary between 200 microamperes and 20 milliamperes, and in a most preferred embodiment may vary between 500 microamperes and 5 milliamperes. The amplitude 66 may be fixed or vary. In some embodiments of the present invention, the amplitude of the cathodic and anodic phases may differ.

The parameters of pre-pulse train 50, primary pulse train 60 and vibrating element 22 may be adapted according to the present state of these respective parameters, the pending state of these respective parameters, and information from impedance monitor 44.

Figure 10:
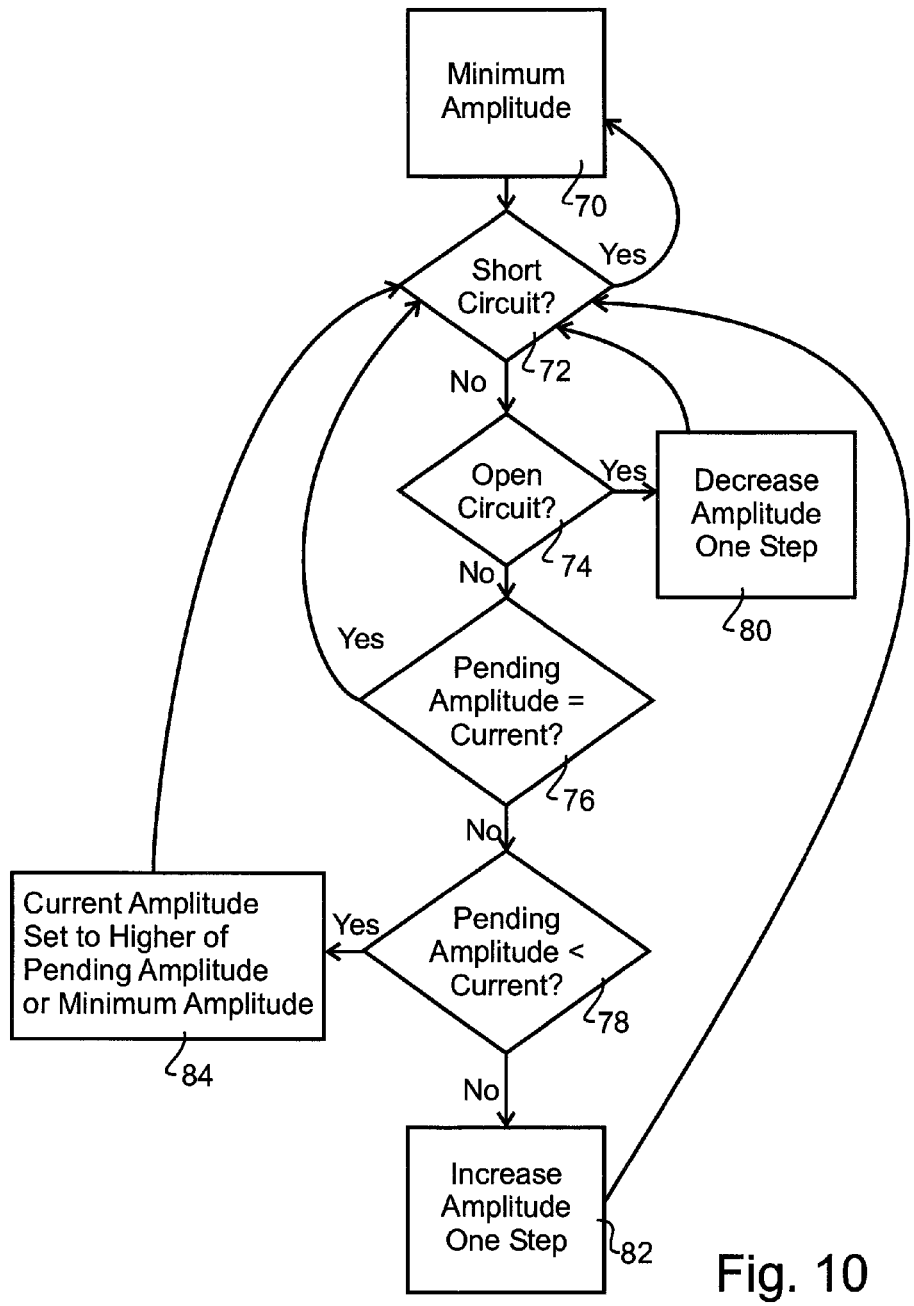
FIG. 10 illustrates a flow chart depicting electrostimulation adjustments that may be made in one embodiment of the present invention in response to the current state, the pending next state and feedback from the tissue impedance monitor.

Referring now to the flow chart in FIG. 10, which is applicable to some embodiments of the present invention, the excitation amplitude, where the excitation may for exemplary purposes comprise vibrational excitation, electrical excitation, or a combination thereof, begins at the minimum amplitude state 70. This minimum amplitude state is most preferred, since there is no risk of tissue harm or the generation of a pain sensation. In one embodiment using digital control and analog to digital conversions, the full-scale stimulation amplitude may be fractionalized into a number of discrete steps. For exemplary purposes, these steps may be such as 8, 16, 32, 64, 128 or 256. Also anticipated by the present invention are other fractional stimulation amplitude steps between 4 and 4096. The system then checks in decision step 72 if a short circuit exists between any of a number of body surface electrodes. If so, the system resorts to minimum amplitude state 70. If not, the system checks in decision step 74 if an open circuit condition exists. If yes, the amplitude of the stimulation element is decreased by a step, but not less than the minimum stimulation amplitude, in step 80 and the system returns to decision step 72. If not, the system then checks in decision step 76 if the pending stimulation amplitude matches the present amplitude. If yes, the system returns to decision state 72. If not, the system checks to see if the pending stimulation amplitude is less than the current amplitude in 78. If yes, the current stimulation amplitude is immediately programmed to the pending stimulation amplitude in step 84 and returns to decision step 72. If not, the stimulation amplitude is increased by one step in 82 and the system returns to decision step 72.

In the preferred embodiment, the amplitude state changes are not made instantaneously. If they were, then the moment an open circuit condition existed, steps 72, 74 and 80 would be processed repeatedly and in an instant, would effectively switch the stimulation amplitude to minimum amplitude upon an open circuit detection. While this would protect a body 6 from a painful stimulation, this would also create a distinct drop-off in stimulation should the user only very briefly lift the electrode.

Instead, in the preferred embodiment the increases and decreases in amplitude are only made after the elapse of a time interval or delay. This delay may be varied or adjusted, or may be fixed at the time of design. Preferably, the delay will be determined such that rate of decrease in stimulation amplitude at least roughly corresponds to rate of increase in sensitivity exhibited by various receptors of interest that are reverting to a resting state. In other words, and only for exemplary and non-limiting purposes, if a receptor takes two seconds to revert to a resting state, in this embodiment the time required for the stimulation amplitude to revert to minimum in an open circuit condition would also be approximately two seconds. As may be apparent then, the amount of time required to drop from a maximum stimulation amplitude to a minimum stimulation amplitude will be the product of the time delay between step adjustments and the total number of steps between maximum and minimum that are provided for in a particular embodiment.

By approximating the time to return to minimum to match the time for a receptor of interest to return to resting state, one of the problems of habituation is addressed. According to the principles of habituation, the body 6 will quickly acclimate to a stimulation amplitude, and the stimulation amplitude will need to be increased to maintain the same perceived level of stimulation. As noted herein above, the preferred waveforms of FIG. 9 reduce this habituation, but nevertheless do not eliminate it entirely. Consequently, if the electrodes are briefly removed from body 6, and then re-applied at the same stimulation amplitude, contact resistance, and electrode location, there is a very high probability that the body 6 will perceive pain. By reducing the stimulation amplitude through steps 72, 74, and 80 to approximately correspond to the increased sensitivity of the receptors, a body 6 will not perceive any change in the level of stimulation. When the electrodes are then re-attached to body 6, habituation will again occur, and to overcome this effect, the stimulation amplitude will again be increased through step 82 in a gradual manner. Once again, the time delay for this increase will preferably approximately correspond to the target receptor habituation.

The flow chart depicted in FIG. 10 is not intended to be limiting in the scope of the present invention, with other state and decision orderings and operations well known in the art of course anticipated by the present invention, as long as the system behavior includes: a return to minimum amplitude stimulation when a short circuit is detected, an immediate decrease in stimulation amplitude to match any pending amplitude setting, a gradual decrease in stimulation amplitude when an open circuit is detected and a gradual increase in stimulation amplitude when the pending amplitude setting exceeds the present amplitude setting.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the use of any particular specific configuration of controller or body surface electrode shown explicitly in the drawings hereof. The embodiments disclosed herein may be implemented with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices. Those skilled in the art will understand immediately that many variations and permutations of known systems for potentiating or eliciting an erotic sensation may be employed successfully in the present invention.

In the claims, means plus function clauses are intended to cover the structures described herein as performing the recited function and their equivalents. Means plus function clauses in the claims are not intended to be limited to structural equivalents only, but are also intended to include structures which function equivalently in the environment of the claimed combination. All printed publications and patents referenced herein above are hereby incorporated by reference herein, each in its respectively entirety.

While the foregoing details what is felt to be the preferred embodiment of the invention, no material limitations to the scope of the claimed invention are intended. Further, features and design alternatives that would be obvious to one of ordinary skill in the art are considered to be incorporated herein. The scope of the invention is set forth and particularly described in the claims herein below.

The invention claimed is:

1. An electrostimulation apparatus, comprising:
   an electrical power source;
   an electrical signal generator coupled with said electrical power source and adapted to operatively generate a biphasic electrostimulation signal having at least one parameter selected to potentiate an erotic sensation in a body,
   said biphasic electrostimulation signal having a primary pulse and a plurality of high frequency pre-pulses prior to, and of narrower pulse width than, said primary pulse so as to reduce concomitant adverse sensation and habituation at the locus of electrostimulation;
   at least one body surface electrode adapted to operatively deliver said electrostimulation signal to at least one portion of a body;
   at least one additional electrode adapted to operatively complete an electrical circuit between said at least one body surface electrode, said body, and said electrical signal generator;
   an impedance monitor adapted to operatively measure an impedance between said at least one body surface electrode and said at least one additional electrode; and
   a stimulation amplitude control adapted to operatively decrease an electrostimulation amplitude of said biphasic electrostimulation signal applied to said body responsive to said impedance indicative of an open circuit between said at least one body surface electrode and said at least one additional electrode.

2. The electrostimulation apparatus of claim 1, wherein said biphasic electrostimulation signal is decreased by said stimulation amplitude control in a stepped manner.

3. A method comprising:
   Generating, via an electrical signal generator, a biphasic electrostimulation signal having at least one parameter selected to potentiate or elicit an erotic sensation in a body;

incorporating a plurality of high frequency pre-pulses prior to, and of narrower pulse width than, a primary pulse in the biphasic electrostimulation signal so as to reduce concomitant adverse sensation or habituation at the locus of electrostimulation; and delivering the electrostimulation signal to at least one portion of a body via at least a body surface electrode, positionable, secured or attached to or on a body surface thereby.

4. The method of claim 3, wherein the locus of electrostimulation is selected from the group comprising hands, feet, lips, face, mouth, breasts, anus, rectum, and genitalia.

5. The method of claim 3, further comprising the step of configuring the electrostimulation signal delivered to said body surface electrodes to vary at least one of a frequency, rate, amplitude, phase, width and morphology of said pulses.

6. The method of claim 3, wherein an amplitude of any pulse in said electrostimulation signal is between about 500 microamperes and 5 milliamperes.

7. The method of claim 3, wherein the electrostimulation signal further comprises a primary pulse train wherein the frequency of any two adjacent primary pulses is between about 1 Hz and about 1 kHz.

8. The method of claim 3, wherein the electrostimulation signal further comprises a primary pulse train wherein the pulse width of any pulses of the primary pulse train is between about 10 microseconds and 5 milliseconds.

9. The method of claim 3, wherein said plurality of high frequency pulses preceding any pulse in the primary pulse train further comprises between about 2 and about 50 high frequency pulses.

10. The method of claim 3, wherein the frequency of said plurality of high frequency pulses preceding any pulse in the primary pulse train is between about 300 Hz and 30 kHz.

11. The method of claim 3, wherein a pulse width of said plurality of high frequency pulses preceding any pulse in the primary pulse train is between about 5 microseconds and about 200 microseconds.

12. The method of claim 3, further comprising the steps of:
measuring impedance between at least any two body surface electrodes; and dropping an electrostimulation signal amplitude to a minimum level responsive to a measured impedance between about 0.01 ohms and about 1000 ohms.

13. The method of claim 3, further comprising the steps of:
measuring impedance between at least any two body surface electrodes; and decreasing an electrostimulation amplitude for subsequent electrostimulation responsive to said measured impedance between at least any two body surface electrodes indicative of an open circuit.

14. The method of claim 13, wherein said step of decreasing said electrostimulation amplitude is done in stepwise manner by about $\frac{1}{4}$th, about $\frac{1}{8}$th, about $\frac{1}{16}$th, about $\frac{1}{32}$nd, about $\frac{1}{64}$th, about $\frac{1}{128}$th or about $\frac{1}{256}$nd of the full-scale electrostimulation amplitude.

15. The method of claim 13, wherein said measured impedance between at least any two body surface electrodes is indicative of an open circuit when greater than about 100 kilo-ohms.

16. The method of claim 3, further comprising the step of increasing the electrostimulation amplitude for subsequent electrostimulation responsive to a pending electrostimulation amplitude exceeding a current electrostimulation amplitude.

17. The method of claim 16, wherein step of increasing said electrostimulation amplitude is done in stepwise manner by about $\frac{1}{4}$th, about $\frac{1}{8}$th, about $\frac{1}{16}$th, about $\frac{1}{32}$nd, about $\frac{1}{64}$th, about $\frac{1}{128}$th or about $\frac{1}{256}$nd of the full-scale electrostimulation amplitude.

18. The method of claim 3, further comprising the step of decreasing the electrostimulation amplitude to match that of a pending electrostimulation amplitude responsive to said pending electrostimulation amplitude being less than a current electrostimulation amplitude.

19. The method of claim 3, further comprising the step of applying a mechanically vibrating element adjacent to a body surface.

20. The method of claim 3, wherein the controller housing the electrostimulation signal generator further comprises at least one of a primary battery power source, a secondary battery power source, and a mains connected power source.

* * * * *